United States Patent [19]

Moses et al.

[11] Patent Number: 5,213,793

[45] Date of Patent: May 25, 1993

[54] HAIR CONDITIONING

[75] Inventors: Ronald E. Moses, Winthrop; Frances M. Roberto, Marblehead, both of Mass.

[73] Assignee: The Gillette Company, Boston, Mass.

[21] Appl. No.: 452,199

[22] Filed: Dec. 18, 1989

Related U.S. Application Data

[63] Continuation-in-part of Ser. No. 226,852, Jul. 27, 1988, abandoned, which is a continuation of Ser. No. 766,832, Aug. 16, 1985, abandoned, which is a continuation of Ser. No. 570,399, Jan. 13, 1984, abandoned.

[51] Int. Cl.$^5$ .............................................. A61K 7/075
[52] U.S. Cl. ...................................... 424/70; 424/71; 424/DIG. 2; 514/938; 132/202
[58] Field of Search ........................... 424/70, 71; 514/937-943, 772; 132/202

[56] References Cited

U.S. PATENT DOCUMENTS

| | | |
|---|---|---|
| 3,208,911 | 9/1965 | Oppliger .............................. 167/87 |
| 3,993,744 | 11/1976 | Cella et al. ........................... 424/70 |
| 4,122,029 | 10/1978 | Gee et al. ............................ 252/309 |
| 4,165,369 | 8/1979 | Watanabe et al. ..................... 424/70 |
| 4,185,087 | 1/1980 | Morlino .............................. 424/70 |
| 4,252,695 | 2/1981 | Homma et al. ....................... 252/547 |
| 4,374,825 | 2/1983 | Bolich et al. ......................... 424/70 |
| 4,551,330 | 11/1985 | Wagman et al. ...................... 424/70 |
| 4,801,447 | 1/1989 | Gum ............................... 514/941 X |

FOREIGN PATENT DOCUMENTS

| | | |
|---|---|---|
| 737438 | 6/1966 | Canada ............................... 167/73 |
| 820275 | 8/1969 | Canada .............................. 167/301 |
| 3029306 | 3/1981 | Fed. Rep. of Germany . |
| 3206448 | 10/1982 | Fed. Rep. of Germany . |
| 1221156 | 2/1971 | United Kingdom . |
| 2066659A | 7/1981 | United Kingdom . |
| 1598567 | 9/1981 | United Kingdom . |
| 2074184A | 10/1981 | United Kingdom . |
| 2102288A | 2/1983 | United Kingdom . |

OTHER PUBLICATIONS

Berger et al., "Hair Conditioners, Lacquers, Setting Lotions, and Rinses", Cosmetics-Science and Technology, vol. 2, pp. 345-352 and 369-372 (1957).
Dow Corning, "Information About Silicone Fluids" Dow Corning Corporation, (brochure) (1978).
Schoenberg et al., "Role of Alkylamidoamine Salts in the Modern Hair Conditioner", Cosmetics & Toiletries, vol. 94, pp. 57-64 (Mar. 1979).
Cannell, "Split Ends and Their Repair", Cosmetics & Toiletries, vol. 94, pp. 29-31, (Mar. 1979).
Breuer et al., "Physical Chemistry of Hair Condition", Cosmetics & Toiletries, vol. 94, pp. 29-34 (Apr. 1979).
"Hair Care Preparations (excluding hair colorants and conventional shampoos) in the patent literature: 1968-1978", Cosmetics & Toiletries, vol. 94, pp. 61-69 (1979).

Primary Examiner—Thurman K. Page
Assistant Examiner—D. Colucci
Attorney, Agent, or Firm—Fish & Richardson

[57] ABSTRACT

A water-in-oil emulsion hair conditioning composition containing no more than about one percent total solids, and at least one cationic hair conditioning agent, the hair conditioning composition preferably comprising from about five to about ten percent of a volatile oil, up to about three percent of a hydrophobic emulsifying agent, from about 0.01% to about 0.5% of the cationic hair conditioning agent, and water.

36 Claims, No Drawings

HAIR CONDITIONING

This application is a continuation-in-part of of pending U.S. application Ser. No. 07/226,852, filed Jul. 27, 1988, now abandoned, which is a continuation of U.S. Ser. No. 06/766,832 now abandoned, filed Aug. 16, 1985, which is a continuation of U.S. Ser. No. 06/570,399, now abandoned filed Jan. 13, 1984.

BACKGROUND OF THE INVENTION

This invention relates to hair conditioning compositions.

Healthy, undamaged hair can be naturally difficult to comb, especially when wet. Damaged hair, such as can result from exposure to excessive heat and dryness (e.g., blow-drying, sun, and wind) and from chemical treatments (e.g., bleaching or coloring and permanents which curl or straighten the hair) can be even more difficult to comb.

Hair conditioners designed to improve the combability of the hair typically contain a cationic composition(s) as the active conditioning ingredient or ingredients that is designed to reduce static as well as generally condition; fatty alcohols, waxes, or resins to provide a thick cream vehicle for the active ingredient(s); proteins; humectants; and various perfunes and preservatives. These ingredients are typically combined either with a hydrophilic emulsifier to produce an oil-in-water emulsion or with a suspending agent or a thickener (e.g. a cellulose gum). In these formulations, the lipophilic part of the active ingredient is in the oil phase which, by the action of the emulsifier or dispersion agent, exists as small droplets within the larger amount of water (the external phase). The external aqueous phase characteristic of these distribution systems has been considered to be a necessary component of hair conditioning compositions since one of the criteria for such compositions is that they must be easily rinsed from the hair after application. Such compositions are relatively inefficient in delivering the active ingredient(s) contained in the oil phase to the hair. Dispersions and oil-in-water emulsions tend to form beads on the hair shafts so the conditioning agents are not uniformly distributed throughout the hair. Further, since the active ingredient is widely dispersed as small droplets within the bead, the bead must be physically worked, e.g., by rubbing the conditioner into the hair, so as to bring the oil phase into contact with the hair shaft. In addition to being an inefficient method of delivering the active ingredient to the hair, such working can further damage or break off already-weakened hair.

Another factor contributing to the inefficiency of typical conditioners is the significant amount of solid (i.e., non-volatile) ingredients used in addition to the key cationic ingredient. Such other ingredients include fatty alcohols, waxes, thickeners, proteins, and the like. The total content of such ingredients in a typical commercially-available conditioner range from about 2.5% to about 10%. Those ingredients tend to deposit on the hair and form a tacky surface which attracts dust and other airborne particulates, causing the hair to become dull-looking and dirty. The surface coating can also give the hair a greasy look and feel. Further, the solids can weigh the hair down (especially after collecting dust and other particulates) leaving the hair flat with no body or fullness.

In general, the invention features a hair conditioning composition consisting of a water-in-oil emulsion containing less than about 0.5%, and preferably no more than about 0.3% of the active ingredient, that active ingredient being dissolved, to a significant extent, in the external oil phase of the emulsion so that it comes into direct contact with the hair upon application. Less than about ten percent, more preferably six–eight percent, of the oil phase is needed. The composition also contains up to about three percent of an emulsifier material. The conditioning composition preferably has a viscosity of from about 1000 to about 8000 centipoises, more preferably a viscosity of from about 4000 to about 6000 centipoises.

Conditioners according to the invention have a thinner texture and a lighter feel than typical high-solids oil-in-water emulsion conditioners. When applied to the hair, the water-phase portion of conditioners according to the invention rinses away easily, leaving the hair with significantly improved combability. During drying, the volatile oil portion of the conditioner evaporates rapidly and with a slight cooling effect, in contrast to the heavy, greasy feeling which often accompanies typical conditioners.

In addition to having a lighter, cleaner feel, conditioners according to the invention are more efficient in delivering the active ingredient (i.e., the cationic hair conditioning agent) to the hair. The external oil phase delivers the conditioner smoothly along the hair shafts, producing a more uniform distribution of the conditioner on the hair. Since the active ingredient (the conditioning agent) is in the external phase, the conditioner does not have to be physically worked to bring the conditioning agent into contact with the hair. Quaternary and/or amine conditioning compounds having an HLB of less than about 12 were found to deliver conditioning benefits with the least oily or greasy feel imparted to the hair. A water-in-oil conditioning emulsion in accordance with the invention functions effectively with a small fraction of the active ingredient usually contained in oil-in-water conditioning emulsions. Little residue is left on the hair after rinsing and drying the hair since the formulations have low total solids contents. While some of the volatile oils remain after rinsing, these evaporate within a short period of time and so do not build up on the hair. The slight amount of residue minimizes the problems of attracting dust, making the hair appear dull or greasy, and weighing the hair down.

Formulations in accordance with the invention impart a greater conditioning effect to the hair than would be expected based solely on the amounts of the active ingredient(s) present, due to the efficiency of delivery. Because of the system delivery efficiency, other solid ingredients can be added; the resulting conditioner still being significantly more effective and efficient than typical oil-in-water emulsions and dispersions in delivering the active ingredient(s) to the hair.

The essential components of formulations according to the present invention, as indicated above, are (1) a volatile oil, (2) an emulsifier which when properly mixed with the remaining components yields a water-in-oil emulsion, (3) a cationic hair conditioning agent which is at least partially soluble in the volatile oil, and (4) a water phase.

Volatile Oil

The volatile oil is selected from the group consisting of liquid silicones and hydrocarbons and mixtures thereof having a measurable vapor pressure, a boiling point at atmospheric pressure from about 95° C. to about 250° C. and a solubility in water of less than about 0.1%. The silicone can be a cyclic polydimethylsiloxane (cyclomethicone) of the general formula:

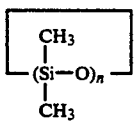

where n=3 to 7, or a linear polydimethyl-siloxane of the general formula:

$(CH_3)_3Si\text{—}O[Si(CH_3)_2\text{—}O]_nSi(CH_3)_3$ where n=1 to 7. Both cyclic and linear silicones as described are available from the Dow Corning Corporation, for example Dow Corning 344 and 345 fluids, from General Electric, for example GE SF 1204, and from other companies. The hydrocarbons may contain from about 7 to about 16 carbon atoms, preferably from 7 to 10, in a linear or branched configuration. Suitable hydrocarbons include heptane, octane, decane, dodecane, tetradecane, tridecane, and mixtures thereof.

Preferred conditioning compositions contain from about 5% to about 10% by weight, of the volatile oil, more preferably from about 6% to about 8%. A preferred volatile oil is a volatile silicone, particularly, the cyclic tetramer of polydimethylsiloxane.

Emulsifier

The emulsifier is a hydrophobic emulsifying agent which will result in a stable water-in-oil emulsion even with a proportionately-large water phase and a low-viscosity oil phase. Suitable emulsifying formulations comprise an organic water-in-oil surfactant which has a hydrophilic-lipophilic balance (HLB) value of from 2 to 10 inclusive and a polydiorgano-siloxanpolyoxyalkylene copolymer. Examples of suitable emulsifying agents are described in Gee et al., U.S. Pat. No. 4,122,029. A preferred emulsifier is Dow Corning DCX2-3225C, which is 90% volatile silicones and 10% dimethicone copolyol.

Conditioner formulations in accordance with the invention contain up to about 3% emulsifier (i.e., 0.3% copolyol and 2.7% volatile silicones), preferably 0.1% to 0.6%, and particular compositions contain about 0.3%.

Cationic Hair Conditioning Agent

Cationic hair conditioning agents used in the present formulations are selected from the group consisting of quaternary ammonium salts, fatty amines and salts thereof.

Suitable quaternary ammonium salts may be of the formula:

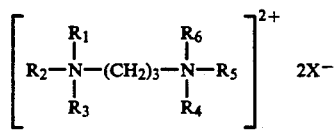

wherein $R_1$ is an aliphatic group having 16 to 22 carbon atoms, $R_2$, $R_3$, $R_4$, $R_5$, and $R_6$ are selected from the group consisting of hydrogen and lower alkyls (1 to 4 carbon atoms), and X is an anion selected from the group which includes halogen, acetate, phosphate, nitrate, and methyl sulfate radicals. An example of such a salt is tallow propanediammonium dichloride.

Quaternary ammonium salts in which the nitrogen atom is part of a cyclic configuration may also be used. For example, the cationic hair conditioning agent could be a quaternary imidazolinium salt of the general formula:

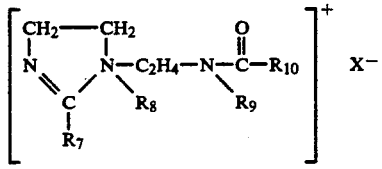

where $R_7$ is hydrogen or an alkyl group containing from 1 to 22 carbon atoms, preferably at least 15, $R_8$ is a lower alkyl (1 to 4, preferably 1 to 2, carbon atoms), $R_9$ is hydrogen or a lower alkyl (1 to 4 carbon atoms), $R_{10}$ is an alkyl group containing from 8 to 22 carbon atoms, preferably at least 15, and X is an anion as described above, preferably chloride. Imidazolinium salts in which both $R_7$ and $R_{10}$ are alkyls containing from 12 to 22 carbon atoms are preferred, e.g., 1-methyl-1-[(stearoylamide)ethyl]-2-heptadecyl-4,5-dihydroimidazolinium chloride and 1-methyl-1-[(palmitoylamide)ethyl]-2-octadecyl-4,5-dihydroimidazolinium chloride.

Preferred cationic hair conditioning agents for use in formulations according to the present invention are quaternary ammonium salts of the formula:

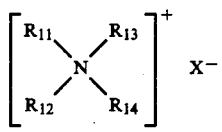

where $R_{11}$ is an aliphatic group of from 1 to 22 carbon atoms, or aromatic or alkaryl groups having from 12 to 22 carbon atoms; $R_{12}$ is an aliphatic group having 1–22 carbon atoms; $R_{13}$ and $R_{14}$ are each alkyl groups of from 1 to 3 carbon atoms, and X is an anion selected from the group which includes halogen, acetate, phosphate, nitrate and methyl sulfate radicals. The aliphatic groups may contain, in addition to carbon and hydrogen atoms, ether linkages as well as amido groups among other groups.

Of this group, the most preferred compounds are alkyl aryl dimethyl ammonium chlorides, wherein the alkyl group has from 12 to 22 carbon atoms and is derived from long-chain fatty acids, such as hydrogenated tallow. ("Tallow" refers to fatty alkyl groups derived from tallow fatty acids.) A particularly preferred cationic conditioning agent is stearyl dimethyl benzyl ammonium chloride (stearalkonium chloride) that has an HLB value of about 11–12.

The fatty amines may be primary, secondary, or tertiary, but are preferably primary. Diamines having a long chain alkyl group may also be used. Examples of suitable amines are dimethyl stearamine, stearylamine, myristylamine, tridecylamine, and ethyl stearylamine. The anions of the salts are from the group which includes halogen, acetate, phosphate, nitrate, and methyl sulfate radicals. A specific amine salt is stearylamine hydrochloride.

Conditioner formulations of the present invention contain from about 0.01% to about 0.5% of the cationic conditioning agent, and particular compositions contain about 0.3%.

Water Phase

The water phase makes up the remainder of the conditioning composition. This phase may be entirely water, preferably distilled water, or it may contain up to about 20% of a physiologically-acceptable alcohol, e.g., ethanol, isopropanol, propylene glycol, or glycerol. The formulations preferably contain less than about 10% alcohol, and particular compositions contain about 5%.

Optional Components

The conditioning composition may include additional, optional components which are soluble in the volatile oil phase or the water phase, or which are not soluble in either phase. For example, perfumes, coloring, buffers, perservatives, opacifiers, proteins, antioxidants, and the like may be added to the composition to impart desirable functional and/or aesthetic stability qualities. Optional components which have high solids contents can be added in small amounts without significantly reducing the efficacy of the conditioning composition. However, the formulation should have a total solids content (constituents that leave a non-volatile residue on the hair) of less than about one percent.

Method of Manufacture

Many methods of combining the ingredients of the hair conditioning compositions of the present invention are available. In general, the water and cationic hair conditioning agent(s) are combined with other water-soluble ingredients (e.g., preservatives) and heated to about 50°±5° C. until the conditioning agent(s) completely dissolves. In a separate vessel, the volatile oil is mixed with the emulsifier, alcohol, if any, and any other oil-soluble additives until uniform. The warm water phase is then slowly added to the oil phase with moderate agitation; the emulsion thickens as the water is added. Fragrance and/or coloring can be added to the resulting emulsion. The cationic hair conditioning agent is initially dispersed or dissolved in warm water as a matter of convenience. Since it is much more soluble in the oil phase, it moves into the oil phase as the two phases are combined.

Use

Hair conditioning compositions of the present invention are preferably used on freshly-shampooed hair. From about 1 gram to about 60 grams of the composition, preferably from about 5 grams to about 30 grams, are applied to the hair, gently worked or combed through to be evenly distributed, and then rinsed from the hair. Alternatively, the composition may be left on the freshly-shampooed hair, or may be applied to dry hair, e.g., by pump-spraying, between shampooing to aid in combing and manageability. Since the solids contents of the compositions are so low, there is minimal residue build-up (with its associated problems) when the compositions are applied by these latter methods.

The following examples illustrate hair conditioning compositions within the scope of the present invention and are not to be construed as limitations thereof. Unless otherwise indicated, all percentages herein are by weight.

EXAMPLE 1

The following composition has an external oil phase of about 10% and was prepared by the general method as set forth above for use as a creme rinse:

| Cyclomethicone (Dow 344) | 7.5% |
| Emulsifier (DCX2-3225C) | 3.0 |
| Stearalkonium chloride | 0.1 |
| Water | q.s. to 100% |

In objective (clinic) testing against a commercially available oil-in-water emulsion conditioner with a conditioning agent content of about 2%, the wet combing, dry combing and detangling attributes of the composition of Example 1 were rated as good as or better than the oil-in-water emulsion conditioner.

EXAMPLE 2

The following composition was prepared by the general method as set forth above for use as a creme rinse:

| Cyclomethicone (Dow 344) | 7.5% |
| Emulsifier (DCX2-3225C) | 3.0 |
| Stearalkonium chloride | 0.1 |
| Phenoxyethanol | 0.2 |
| Methyl paraben | 0.2 |
| Frangrance and Dyes | 0.2 |
| Water | q.s. to 100% |

This composition was prepared as in Example 1, modified by adding the phenoxyethanol and methyl paraben to the aqueous phase prior to mixing with the oil phase.

EXAMPLE 3

The following hair conditioner composition was prepared according to the method as set forth in Example 2:

| Cyclomethicone (Dow 344) | 7.0% |
| Emulsifier (DCX2-3225C) | 3.0 |
| Fragrance | 0.3 |
| Phenoxyethanol | 0.2 |
| Methyl paraben | 0.2 |
| Stearalkonium chloride | 0.1 |
| Water | q.s. to 100% |

EXAMPLE 4

The following hair conditioner composition was prepared by combining the cyclomethicone, ethanol, phenoxyethanol, methyl paraben, and dimethicone copolyol; dissolving the stearalkonium chloride in water heated to about 50° C. and adding the water phase to the oil phase; and adding the fragrance to the finished emulsion:

| Cyclomethicone (Dow 344) | 6.0% |
| Ethanol (SD-40) | 5.0 |
| Emulsifier (DCX2-3225C) | 3.0 |
| Fragrance | 0.3 |
| Phenoxyethanol | 0.2 |
| Methyl paraben | 0.2 |

| | |
|---|---|
| Stearalkonium chloride | 0.1 |
| Water | q.s. to 100% |

EXAMPLE 5

The following hair conditioner composition was prepared according to the method as set forth in Example 4:

| | |
|---|---|
| Cyclomethicone (Dow 344) | 6.0% |
| Ethanol (SD-40) | 5.0 |
| Emulsifier (DCX2-3225C) | 3.0 |
| Fragrance | 0.3 |
| Phenoxyethanol | 0.2 |
| Methyl paraben | 0.2 |
| Stearalkonium chloride | 0.01 |
| Water | q.s. to 100% |

In objective (clinic) testing against a commercially available oil-in-water emulsion conditioner with a conditioning agent content of about 2%, the wet combing, dry combing and detangling attributes of the composition of Example 5 were rated as good as or better than the oil-in-water emulsion conditioner.

EXAMPLE 6

The following hair conditioner composition was prepared according to the method as set forth in Example 4, modified by adding the panthenol to the water phase prior to mixing:

| | |
|---|---|
| Cyclomethicone (Dow 344) | 6.0% |
| Ethanol | 5.0 |
| Emulsifier (DCX2-3225C) | 3.0 |
| Panthenol | 0.3 |
| Fragrance | 0.3 |
| Phenoxyethanol | 0.2 |
| Methyl Paraben | 0.2 |
| Stearalkonium Chloride | 0.1 |
| Water | q.s. to 100% |

EXAMPLE 7

The following hair conditioner composition was prepared according to the method as set forth in Example 4:

| | |
|---|---|
| Cyclomethicone (Dow 344) | 6.0% |
| Ethanol | 5.0 |
| Emulsifier (DCX2-3225C) | 3.0 |
| Fragrance and Preservative | 0.2 |
| Dimethyl di(hydrogenated tallow) ammonium chloride (Adogen 442) | 0.5 |
| Water | qs. to 100% |

EXAMPLE 8

The following hair conditioner composition was prepared according to the method as set forth in Example 4, and had an external oil phase of about 8%:

| | |
|---|---|
| Cyclomethicone (GE SF 1204) | 6.0% |
| Ethanol | 5.0 |
| Emulsifier (DCX2-3225C) | 2.5 |
| Fragrance and Preservative | 0.4 |
| Stearalkonium chloride | 0.3 |
| Water | q.s. to 100% |

EXAMPLE 9

The following hair conditioner composition was prepared according to the method as set forth in Example 4, and had an external oil phase of about 8%:

| | |
|---|---|
| Cyclomethicone (DOW 344) | 6.0% |
| Isopropyl Alcohol | 6.5 |
| Emulsifier (DCX2-3225C) | 2.5 |
| Fragrance and Preservative | 0.2 |
| Stearalkonium chloride | 0.3 |
| Water | q.s. to 100% |

EXAMPLE 10

The following hair conditioner composition was prepared according to the method as set forth in Example 4, and had an external oil phase of about 8%:

| | |
|---|---|
| Cyclomethicone (Dow 344) | 6.0% |
| Ethanol | 5.0 |
| Emulsifier (DCX2-3225C) | 2.5 |
| Fragrance and Preservative | 0.2 |
| Stearalkonium chloride | 0.3 |
| Water | q.s. to 100% |

In objective (clinic) testing against a commercially available 'low-solids' oil-in-water emulsion conditioner with a conditioning agent content of about 0.65%, the wet combing, dry combing and detangling attributes of the composition of Example 10 were rated as good as or better than the oil-in-water emulsion conditioner.

EXAMPLE 11

The following hair conditioner composition was prepared, and had an external oil phase of about 8%:

| | |
|---|---|
| Cyclomethicone (Dow 344) | 6.0% |
| Ethanol | 5.0 |
| Emulsifier (DCX2-3225C) | 2.5 |
| Fragrance and Preservative | 0.4 |
| Stearalkonium chloride | 0.3 |
| Water | q.s. to 100% |

The formulation according to Example 11 was compared with a 'low-solids' oil-in-water emulsion conditioner currently on the market (conditioner content of about 0.65% and solids content of about 2.7%), using the following standard combometer test with an Instron testing machine that had a comb mounted on the crosshead of the testing machine. Each hair tress to be tested is mounted on grips suspended from the Instron tension cell. The comb is pulled through the hair tress by the Instron crosshead, and the force required to perform this task is recorded. The crosshead, adjusted to comb 4.75 inches of a five inch tress, was set to a speed of 20 inches/min. Ten two-times bleached tresses were combed immediately following individual shampooing. The wet tresses were combed fifteen times, and the work of combing for the last seven combings was averaged. The reciprocal of the averaged work was calculated and designated as the combing ease. The wet combed tresses were allowed to dry. The ten tresses were again individually shampooed and were then treated with one of the conditioners. Immediately following conditioning, the tresses were again combed as before. The results of the comparison are set forth in Table 1.

TABLE 1

| Conditioner | Combing Ease* ($gm^1$-$cm^{-1}$) | |
| --- | --- | --- |
| | Without Conditioner | With Conditioner |
| 'Low solids' conditioner | $8.1 \times 10^{-3}$ | $34.0 \times 10^{-3}$ |
| Formulation of Example 11 | $8.8 \times 10^{-3}$ | $37.2 \times 10^{-3}$ |

*Average of five tresses.

Since the combing ease is the reciprocal of the work required to comb the tress, the larger the number the more effective the conditioner in enhancing the combability of hair. These results suggest that formulations according to the invention impart equivalent or better wet combing benefits than the commercial 'low-solids' conditioner, which has approximately four times as much solids as the formulation of Example 11.

While particular embodiments of the invention have been shown and described, various modifications will be apparent to those skilled in the art, and therefore it is not intended that the invention be limited to the disclosed embodiments or to details thereof and departures may be made therefrom within the spirit and scope of the invention.

What is claimed is:

1. A hair conditioning composition in the form of a water-in-oil emulsion that contains no more than about one percent by weight total solids, comprising a volatile oil selected from the group consisting of hydrocarbons, silicones, and mixtures thereof, said volatile oil having a boiling point at atmospheric pressure from about 95° C. to about 250° C., a hydrophobic emulsifying agent and a cationic hair conditioning agent in said oil, said cationic hair conditioning agent being selected from the group consisting of quaternary ammonium salts, fatty amines and salts thereof, the amount of the oil phase of said water-in-oil emulsion being in the range of from about five to about ten percent by weight, the amount of said emulsifying agent being in the range from about 0.1 percent by weight to about 3 percent by weight of said composition, the amount of said cationic hair conditioning agent being in the range from about 0.01 to about 0.5 percent by weight of said composition, and the water phase of said emulsion comprising water.

2. The composition of claim 1 wherein said composition has a viscosity of from about 1000 to about 8000 centipoises.

3. The composition of claim 2 wherein said composition comprises from about six percent to about eight percent by weight of said volatile oil, from about 0.01 to about 0.5 percent by weight of said cationic conditioning agent, and from about 0.1 to about 0.6 percent by weight of said hydrophobic emulsifying agent.

4. The composition of claim 1 wherein said volatile oil is a silicone, and said composition contains about 0.3 percent by weight of said conditioning agent.

5. The composition of claim 1 wherein said cationic hair conditioning agent has an HLB of less than about 12, and the amount of the oil phase of said water-in-oil emulsion is in the range of from about six to about eight percent by weight.

6. A hair conditioning composition in the form of a stable water-in-oil emulsion that contains no more than one percent by weight total solids, comprising
from six percent to eight percent by weight of a volatile silicone oil,
from 0.01 percent to about 0.5 percent by weight of a cationic hair conditioning agent in said oil phase, said cationic hair conditioning agent being selected from the group consisting of quaternary ammonium salts, fatty amines and salts thereof, said cationic hair conditioning agent having a hydrophilic-lipophilic balance value of less than about 12, and
from 0.1 percent to less than 0.8 percent by weight of a hydrophobic emulsifying agent,
the water phase of said emulsion comprising water.

7. The composition of claim 6 wherein said volatile silicone oil has a boiling point at atmospheric pressure from about 95° C. to about 250° C., said emulsifying agent is an organic water-in-oil surfactant which has a hydrophilic-lipophilic balance value of from 2 to 10 inclusive, and said composition has a viscosity of from about 4000 to about 6000 centipoises.

8. A hair conditioning composition in the form of a stable water-in-oil emulsion that contains no more than one percent by weight total solids, comprising
a volatile oil phase comprising a volatile oil selected from the group consisting of liquid silicones and hydrocarbons and mixtures thereof, said volatile oil having a boiling point at atmospheric pressure from about 95° C. to about 250° C.,
a water phase,
a cationic hair conditioning agent in said oil phase, said cationic hair conditioning agent being selected from the group consisting of quaternary ammonium salts, fatty amines and salts thereof and having a hydrophilic-lipophilic balance value of less than about twelve, and
an emulsifying agent;
the amount of the cationic hair conditioning agent in the composition being in the range of from about 0.01 to about 0.05 percent by weight, the amount of said emulsifiying agent in the composition being in the range from about 0.1 percent to about 3 percent by weight, and the amount of said oil phase in the composition being from about five percent to about ten percent by weight of said composition.

9. The composition of claim 8 wherein said composition comprises from about six percent by weight to about eight percent by weight of said volatile oil, and 0.1 to 0.6 percent by weight of said emulsifying agent.

10. The composition of claim 9 wherein said composition has a viscosity of from about 4000 to about 6000 centipoises.

11. A hair conditioning composition in the form of stable water-in-oil emulsion that contains no more than one percent by weight total solids, comprising
a volatile oil selected from the group consisting of liquid silicones and hydrocarbons and mixtures thereof, said volatile oil having a boiling point at atmospheric pressure from about 95° C. to about 250° C.,
a water phase,
a cationic hair conditioning agent in said oil phase, said cationic hair conditioning agent being selected from the group consisting of quaternary ammonium salts, fatty amines and salts thereof, having an HLB value of less than about twelve, and
an emulsifying agent;

the amount of said cationic hair conditioning agent in the composition being in the range from about 0.01 to about 0.5 percent by weight, the amount of said emulsifying agent in the composition being in the range from about 0.1 percent to about 3 percent by weight, and the amount of said oil phase in the composition being from about five percent to about ten percent by weight of said composition.

12. The composition of claim 11 wherein said volatile oil is selected from the group consisting of a cyclic polydimethyl-siloxane (cyclomethicone) of the general formula:

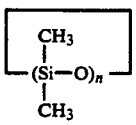

where n=3 to 7, and a linear polydimethyl-siloxane of the general formula:

where N=1 to 7, and said composition contains about 0.3 percent by weight of said conditioning agent, and five to ten percent by weight of said volatile oil.

13. The composition of claim 11 wherein said volatile oil is a hydrocarbon that contains from 7 to 10 carbon atoms in a linear or branched configuration.

14. The composition of claim 11 wherein said composition contains from about six to about eight percent by weight of said volatile oil.

15. The composition of claim 12 wherein said volatile oil is a volatile silicone and includes the cyclic tetramer of polydimethylsiloxane.

16. The composition of claim 7 wherein said emulsifying agent is an organic water-in-oil surfactant which has a hydrophilic-lipophilic balance value of from 2 to 10 inclusive.

17. The composition of claim 16 wherein said composition contains less than 0.6 percent by weight emulsifier.

18. The composition of claim 7 wherein said composition contains about 0.3 percent by weight of said cationic hair conditioning agent.

19. The composition of claim 18 wherein said cationic hair conditioning agent is a quaternary ammonium salt of the formula:

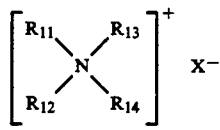

where $R_{11}$ is an aliphatic group of from 1 to 22 carbon atoms, or aromatic or alkaryl groups having from 12 to 22 carbon atoms; $R_{12}$ is an aliphatic group having 1-22 carbon atoms; $R_{13}$ and $R_{14}$ are each alkyl groups of from 1 to 3 carbon atoms, and X is an anion selected from the group consisting of halogen, acetate, phosphate, nitrate and methyl sulfate radicals.

20. The composition of claim 19 wherein said cationic conditioning agent is stearyl dimethyl benzyl ammonium chloride.

21. The composition of claim 17 wherein said composition contains about 0.3 percent by weight of said cationic conditioning agent.

22. The composition of claim 21 wherein said water phase contains up to about twenty percent by weight of a physiologically acceptable alcohol.

23. The composition of claim 21 wherein said composition has a viscosity of from about 4000 to about 6000 centipoises, said volatile oil phase is selected from the group consisting of liquid silicones and hydrocarbons and mixtures thereof and having a boiling point at atmospheric pressure from about 95° C. to about 250° C., and said emulsifying agent is an organic water-in-oil surfactant which has a hydrophilic-lipophilic balance value of from 2 to 10 inclusive.

24. The composition of claim 23 wherein said cationic hair conditioning agent comprises a quaternary compound that has a hydrophilic-lipophilic balance value of about eleven, and said composition contains no more than about eight percent by weight of said volatile oil.

25. A method of conditioning hair comprising
applying to freshly shampooed hair from about one gram to about sixty grams of a composition in the form of a stable water-in-oil emulsion that contains less than one percent by weight total solids, a volatile oil phase comprising a volatile oil in the amount of from about five percent by weight to less than ten percent by weight of said composition, said volatile oil being selected from the group consisting of liquid silicones and hydrocarbons and mixtures thereof and having a boiling point at atmospheric pressure from about 95° C. to about 250° C., a water phase, a cationic hair conditioning agent in said oil phase, said cationic hair conditioning agent being selected from the group consisting of quaternary ammonium salts, fatty amines and salts thereof, and an emulsifying agent comprising from about 0.1 percent by weight to about three percent by weight of said composition.

26. The method of claim 25 wherein said composition contains about 0.3 percent by weight of said conditioning agent.

27. The method of claim 26 wherein said cationic hair conditioning agent comprises stearalkonium chloride, and about eight percent by weight of said volatile oil.

28. The method of claim 25 wherein said composition contains of about 0.3 percent by weight of said conditioning agent, and up to about two percent of said emulsifying agent.

29. The method of claim 26 wherein said volatile oil is a liquid silicone and has a boiling point at atmospheric pressure from about 95° C. to about 250° C.

30. A method of conditioning hair comprising
applying to freshly-shampooed hair from about one gram to about sixty grams of a composition in the form of a stable water-in-oil emulsion that contains a volatile oil phase, comprising a volatile oil in the amount of from about five percent by weight to less than ten percent by weight of said composition, said volatile oil being selected from the group consisting of liquid silicones and hydrocarbons and mixtures thereof, and having a boiling point at atmospheric pressure from about 95° C. to about 250° C., a water phase, a cationic hair conditioning agent in said oil phase, said cationic hair conditioning agent being selected from a group consisting of quaternary ammonium salts, fatty amines, and salts thereof, and an emulsifying agent, said composition containing no more than one percent by weight total solids, no more than about three percent by weight of said emulsifying agent, and less than about 0.5 percent by weight of said conditioning agent; and rinsing the composition from the hair.

31. The method of claim 30 wherein said cationic hair conditioning agent is stearyl dimethyl benzyl ammonium chloride.

32. The method of claim 30 wherein said composition has a viscosity from about 1,000 to about 8,000 centipoises, and said composition comprises from about six percent to about eight percent by weight of said volatile oil, about 0.3 percent by weight of said cationic conditioning agent, and 0.1 to 0.6 percent by weight of said emulsifying agent.

33. The method of claim 30 wherein said volatile oil is a silicone, said cationic hair conditioning agent has an HLB of less than about 12, and the amount of the oil phase of said water-in-oil emulsion is in the range of from about six to about eight percent by weight.

34. A hair conditioning composition in the form of a stable water-in-oil emulsion that contains no more than one percent by weight total solids, comprising more than one percent by weight total solids, comprising from about five to about ten percent by weight of a volatile oil, said volatile oil being selected from the group consisting of liquid silicones and hydrocarbons and mixtures thereof, and having a boiling point at atmospheric pressure from about 95° C. to about 250° C., about 0.3 percent by weight of a cationic hair conditioning agent selected from the group consisting of quaternary ammonium slats, fatty amines and salts thereof in said oil, and a hydrophobic emulsifying agent comprising from about 0.1 percent by weight to about three percent by weight of said composition, the water phase of said emulsion comprising water.

35. The composition of claim 34 wherein said oil phase comprises less than about eight percent by weight of said composition, said cationic hair conditioning agent comprises stearalkonium chloride, and said emulsifying agent comprising from 0.1 percent to 0.6 percent by weight of said composition.

36. The composition of claim 34 wherein said emulsifying agent is an organic water-in-oil surfactant which has a hydrophilic-lipophilic balance value of from about 2 to 10 inclusive, and said composition contains 0.1 to 0.6 percent by weight of said emulsifying agent.

* * * * *